United States Patent [19]

Ackland

[11] Patent Number: 4,801,546

[45] Date of Patent: * Jan. 31, 1989

[54] APPARATUS FOR DETECTING MICRO-ORGANISMS

[75] Inventor: Martin R. Ackland, Wantage, England

[73] Assignee: Metal Box Public Limited Company, Reading, England

[ * ] Notice: The portion of the term of this patent subsequent to Aug. 31, 2004 has been disclaimed.

[21] Appl. No.: 709,035

[22] PCT Filed: Jun. 28, 1984

[86] PCT No.: PCT/GB84/00235

§ 371 Date: Feb. 25, 1985

§ 102(e) Date: Feb. 25, 1985

[87] PCT Pub. No.: WO85/00225

PCT Pub. Date: Jan. 17, 1985

[30] Foreign Application Priority Data

Jun. 29, 1983 [GB] United Kingdom ................ 8317685

[51] Int. Cl.⁴ ............................................... C12M 1/34
[52] U.S. Cl. ........................................ 435/291; 435/34; 435/173; 435/300; 422/102; 324/71.1
[58] Field of Search ............ 435/34, 173, 291, 299–301; 422/73, 99, 102; 436/69, 150; 204/403, 406, 412; 324/62, 71.1, 439, 450; 364/497, 499

[56] References Cited

U.S. PATENT DOCUMENTS

| | | | |
|---|---|---|---|
| 3,883,308 | 5/1975 | Matte | 23/259 |
| 3,890,201 | 6/1975 | Cady | 435/291 |
| 4,009,078 | 2/1977 | Wilkins et al. | 435/34 |
| 4,156,180 | 5/1979 | Annen et al. | 324/71.1 |
| 4,200,493 | 4/1980 | Wilkins et al. | 435/291 |
| 4,250,266 | 2/1981 | Wade | 435/291 |
| 4,321,322 | 3/1982 | Ahnell | 435/34 |
| 4,388,166 | 6/1983 | Suzuki et al. | 204/403 |

FOREIGN PATENT DOCUMENTS 7720114  6/1977  France .

Primary Examiner—Samuel Scott
Assistant Examiner—Noah Kamennk
Attorney, Agent, or Firm—Diller, Ramik & Wight

[57] ABSTRACT

Apparatus for use in detecting micro-organisms in any one of a plurality of samples of a liquid, such as a food or drink product, e.g. for control of production, comprises a plurality of containers (11) for the sample and a container-mounting member (10) to receive and locate each of the containers, each container being provided with a first electrode of a noble metal (16) and a second electrode, which may be constituted by the body of the container (11), insulated from the first and of a different metal. The container-mounting member (10) is provided with separate contacts (12) and leads for each of the noble metal electrodes (16) and with contacts (922) connected to a common lead for each of the second electrodes. The noble metal electrodes (16) are connected to separate terminals of multiplexing recorder system (40) incorporating a micro-processor (41) for testing the signals to ascertain whether the voltage of the noble metal electrode has dropped below a predetermined value, and if so to display particulars.

8 Claims, 3 Drawing Sheets

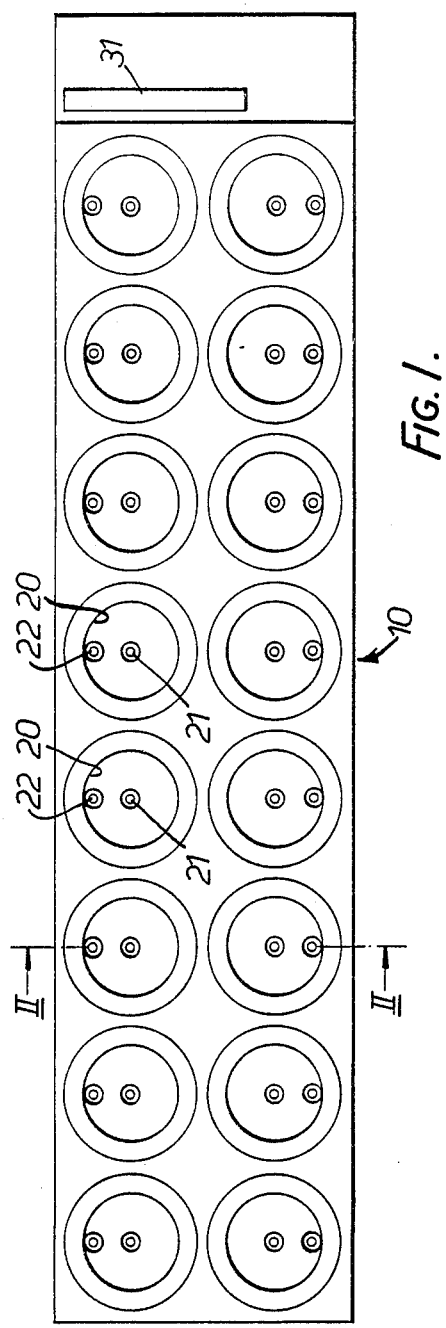
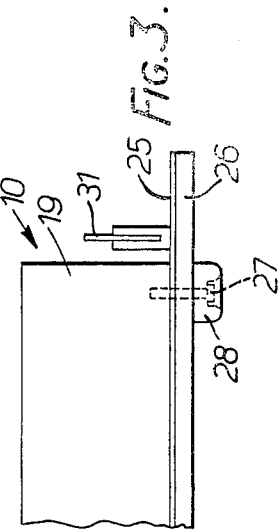
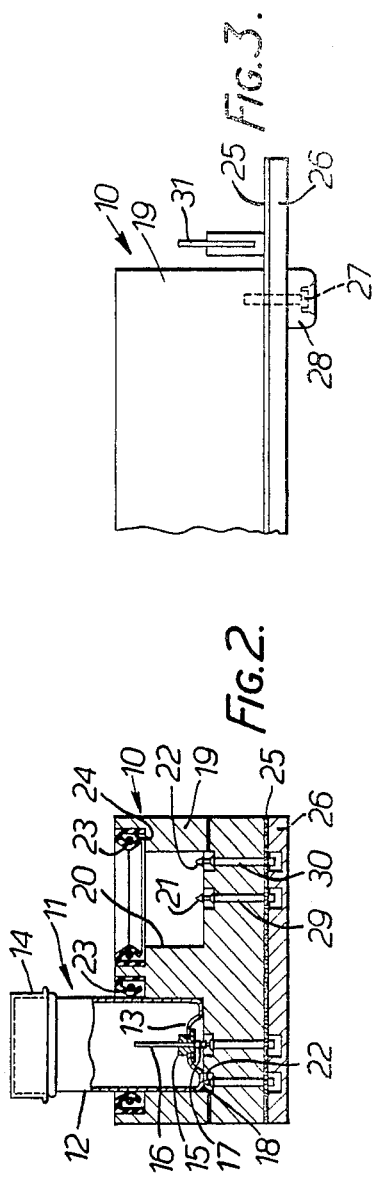

APPARATUS FOR DETECTING MICRO-ORGANISMS

BACKGROUND OF THE INVENTION

This invention relates to apparatus for detecting micro-organisms in samples of a substance. The apparatus can be used, for example for monitoring products intended for human consumption, such as foods, drinks or pharmaceuticals, or may be used to monitor samples in pathological or other laboratories.

DESCRIPTION OF THE RELATED ART

It is known that the growth of micro-organisms in fluid samples can be detected by measuring the changing potential between electrodes in contact with the fluid sample, and apparatus comprising a battery of cells with a multiplexing recorder has been previously described in the literature, together with the use of a micro-processor to monitor the electrical potentials and record voltage changes from the battery of sample cells. It has been observed that when the growth of the micro-organisms reaches a particular stage, the potential shows a marked change, e.g. a steep fall, which may be due to migration and accumulation of the micro-organisms around one of the electrodes.

SUMMARY OF THE INVENTION

An object of the present invention is to provide a particulary simple and effective apparatus for use in detecting micro-organisms in any one of a plurality of samples of a substance, which may for example be a liquid or a mixture of liquid and solid materials, or even a solid such as a solid agar medium.

According to the present invention, such apparatus comprises a plurality of containers for the samples and a container-mounting member with means for receiving and locating each of the containers, characterised in that each container includes a first electrode of a noble metal and a second electrode of a different metal insulated from the first electrode, the electrodes being arranged so as to be contactable with a sample in the container, and presenting respective contact surfaces externally of the container, and characterised in that the container-mounting member is provided with a first set of contacts adapted to engage the external contact surfaces of the containers which correspond with the noble metal electrodes and with a separate lead from each of the said first set of contacts for connecting the noble metal electrodes to separate terminals of a multiplexing recorder system, and a second set of contacts adapted to make contact with the external contact surfaces of the containers which correspond with the second electrodes, all said second set of contacts being connected to a common lead for connecting said second electrodes to a common terminal of the multiplexing recorder system.

Suitably, the containers each comprise a container body formed at least in part of said different metal, and that part of the container body constitutes the respspective second electrode.

Each container may have an upwardly domed bottom through which projects a pin made of or coated with noble metal, constituting the first electrode. Alternatively, each container may have a pin made of or coated with noble metal projecting through its side and constituting the first electrode. Preferably each container has a body of aluminium and the pin constituting the first electrode is gold plated.

In alternative embodiments, each container comprises a closure, the first and second electrode of each container being provided in the respective container closure to extend therethrough.

Where the second electrode is constituted by the part of the container body made of said different metal, the first electrode may be provided in the container closure to extend through.

With these constructions, a set of simple and relatively inexpensive standard containers can be used in a practical and convenient manner for monitoring the samples. The electrode system is relatively simple and, where an aluminium container (which may be of a commercially available standard pattern) is used with a gold plated pin, a substantial potential difference is obtained, making measurement easier. The multiplexing recorder system can be arranged to provide a signal which will identify any container which shows a marked departure from the standard potential, e.g. a steep fall, which will indicate that the growth of micro-organisms in the sample contained therein has reached a particular value. The time taken by the sample to reach this value is a measure of the number of micro-organisms present in the substance from which the sample was taken.

Preferably the container-mounting member comprises a block with recesses each of which is adapted to receive and locate an individual container and is provided with one of each of said two sets of contacts. The container-mounting block preferably has attached to its underside a printed circuit board with leads connecting each of said first set of contacts to an individual contact of a multi-way connector and with leads connecting all of said second set of contacts to a common contact of the multi-way connector.

BRIEF DESCRIPTION OF THE DRAWINGS

FIG. 1 is a plan view of a container-mounting member

FIG. 2 is a cross-section of the member of FIG. 1 on line II—II, showing a first embodiment of a container in position, partly in section FIG. 3 is a detailed view showing an elevation of one end of the container-mounting member (the right hand end in FIG. 1)

DESCRIPTION OF THE PREFERRED EMBODIMENTS

Figure 4:
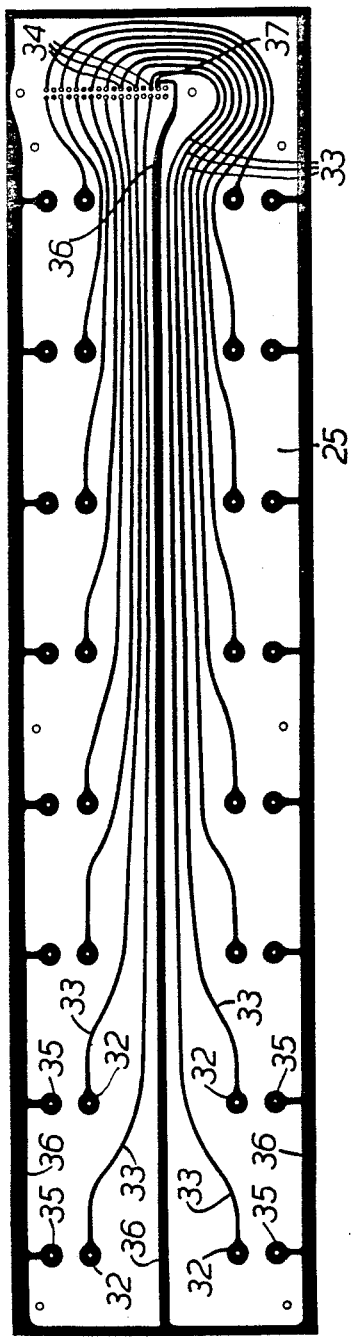
FIG. 4 is a plan of a printed circuit board forming part of the container-mounting member.

As seen in FIGS. 1, 2 and 3, the apparatus comprises a container-mounting member 10 and a plurality of containers, such as that shown at 11 in FIG. 2, of standard shape and size. As shown, the container 11 has a cylindrical body 12 with an integral upwardly domed bottom 13, formed of extruded aluminium, with a screw cap 14. The domed bottom 13 is formed with a central aperture closed by an insulating grommet 15 of rubber or plastics material, through which projects a gold plated pin 16 forming the first electrode. The lower end 17 of the pin 16 is enlarged to form an external contact. The aluminium container body 12 itself forms the second electrode and the annular external surface 18 of its bottom, around the outside of the domed portion 13, forms a corresponding contact area.

The container-mounting member 10 comprises a block 19 formed with a plurality (16 as shown) of cylindrical recesses 20, each of which is adapted to receive and locate an individual container 11 and is provided with two contacts 21, 22 in its bottom surface. To assist in holding the containers 11 in the recesses 20, each recess has a resilient sealing member 23 accommodated in an enlarged upper part 24 of the recess so as to grip the external surface of the body 12 of the container when it is inserted into the recess 20.

The container-mounting member 10 also comprises a printed circuit board 25 secured to the underside of the block 19 by means of a base cover 26 and screws 27 (FIG. 3) which also secure rubber feet 28. The contacts 21, 22 in each recess 20 are spring-mounted and connected through respective vertical bores 29, 30 to the printed circuit board 25. At one end (the right hand end as shown in FIGS. 1 and 3) of the container-mounting member 10, the printed circuit board 25 is exposed and provided with a standard type of 34-way connector 31.

The design of the printed circuit board 25 is illustrated in FIG. 4. Contacts 32 correspond with the contacts 21 at the centre of each recess 20 which connect with the first or noble metal electrodes 16 of each container 11, and each of these contacts 32 has a separate lead 33 leading to an individual contact 34 of the connector 31. Contacts 35 on the printed circuit board 25 correspond with contacts 22 in the recesses 20 and are connected to a common lead 36 leading to a common contact 37 in the connector 31.

Figure 5:
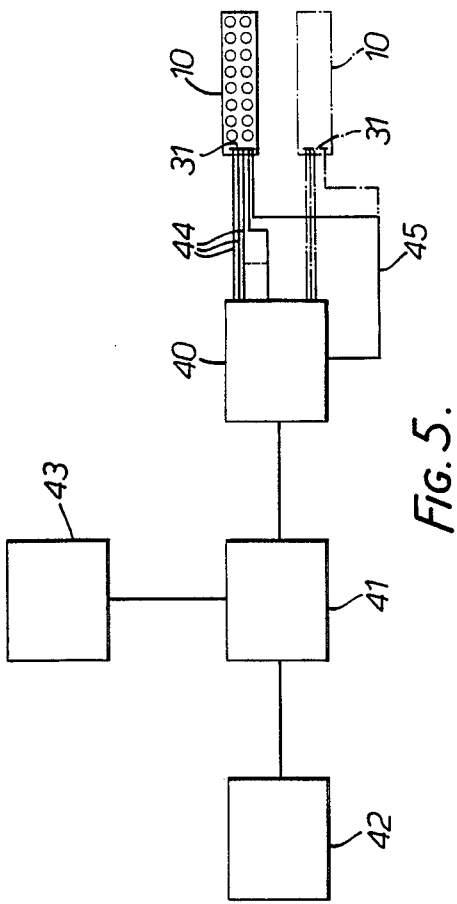
FIG. 5 is a block diagram of the whole apparatus

As shown in FIG. 5, one or more of the container-mounting members 10 is or are connected to a multiplexing recorder system comprising an analogue to digital multiplexing 40 and a micro-processor 41 connected to a visual display unit or printer 42 and a data source 43. The signals from the noble metal electrodes 16 of the containers 11 are fed into the multiplexer 40 via individual leads 44 connected to the terminals 34 of the connector 31. whereas the body 12 of each container, forming the second electrode, is connected via the common terminal 37 of the connector 31 to a common lead 45. The multiplexer 40 may be for example a 128-way unit allowing connection to eight container-mounting members 10 of the kind shown in FIGS. 1 to 4. The multiplexer 40 should have a high input impedance, e.g. of around 10 megohms, or alternatively a resistor of this order to magnitude should be connected between each signal line 44 and the common line 45, for a purpose which will be described later.

For monitoring a series of samples of a liquid, e.g. in the control of the manufacture of a food or drink product, standard size samples are placed in containers 11, which are closed by means of screw caps 14 to exclude contamination, and the containers are placed in respective recesses 20 of the container-mounting member 10 so that their gold electrodes 16 make contact with contacts 21 and the bodies 12 make contact with contacts 22. The multiplexer 40 switches the outputs of the cells constituted by containers 11 to the micro-processor 41 in turn. The micro-processor records the voltages from each container 11 in turn and stores the data together with the time the measurement was taken in the data store unit 43. A visual record can be provided by the visual display unit or printer 42. The micro-processor 41 also makes a test on the voltage level from each container 11 to determine if the voltage has dropped below a predetermined value, say 300 mV. If the voltage is found to have dropped below 300 mV for two consecutive measuring cycles, a note of the corresponding container and the time from commencement of test to detection of the drop in voltage will be recorded and displayed on the visual display unit or on the printout from the printer.

Figure 6:
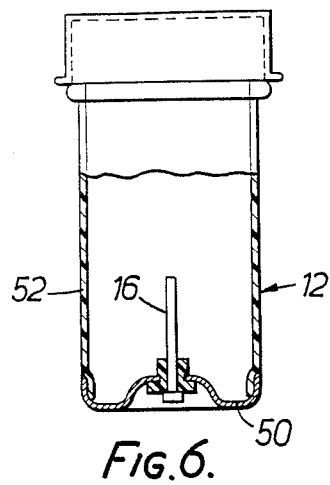
FIG. 6 shows a second embodiment of the container partly in cross-section

FIGS. 6 to 10 each show alternative embodiments of the container. In FIG. 6, the container body 12 has only a base portion 50 made of aluminium, with its cylindrical wall 52 being made of a transparent material e.g. plastics. The base portion 50 forms the second electrode and the sample is now visible in the container.

Figure 7:
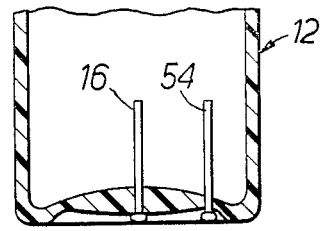
FIGS. 7 and 8 are partial view of third and fourth embodiments of container

In FIG. 7, the entire container body is of a transparent material, e.g. plastics, the second electrode being constituted by an aluminium probe 54 extending through the domed base of the body 12.

Figure 8:
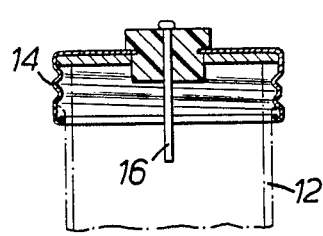
Figure 9:
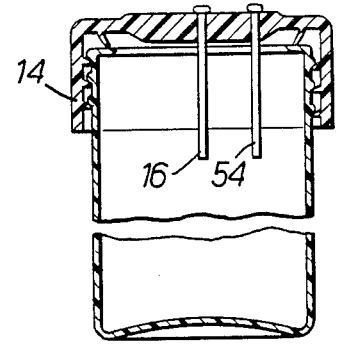
FIG. 9 is a fifth embodiment of container.
Figure 10:
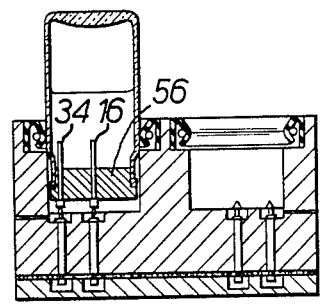
FIG. 10 shows a sixth embodiment of container located in the container-mounting member.

FIGS. 8 to 10 show forms of the container where the electrode or electrodes which are in the form of a probe is or are provided in a closure for the container, which is, for FIG. 8, a metal screw cap 14, for FIG. 9, a plastics screw-cap 14 and for FIG. 10, a rubber bung 56.

It may be desirable to keep the sample out of contact with the electrode(s) until the test is due to start and, by arranging the electrode in the lid, the sample can be stored with the container the right way up, and the test started by inverting the container and inserting it in the container-mounting member 10 when ready.

In FIG. 8, part or all the container body is of metal and constitutes the second electrode while, for FIGS. 9 and 10, the second electrode is a probe 54. The container in FIG. 10 is a conventional glass jar or bottle.

In each case, the first and second electrode are electrically insulated from one another, either by an insulating grommet 15 or by the plastics or glass of the container body itself.

In all cases, the apparatus is arranged so that the container can be inserted in a recess 20 with the noble metal and the second electrodes invariable correctly located to contact their respective contacts 21, 22, for instance by the first electrode being centrally disposed in the closure or base of the container and the second electrode offset from the central axis of the container.

It is known that the voltage measured at a noble metal electrode in a solution containing micro-organisms will show a marked fall when the number of micro-organisms in the solution reaches a particular figure. The apparatus thus provides a convenient method of detecting the growth of micro-organisms in the samples and, by recording the time taken for the natural growth of micro-organisms in the sample to reach a particular level, it gives a good indication of the number of micro-organisms in the product sampled.

The noble metal electrode 16 of each container is connected to the body 12 of the container through the high input impedance of the multiplexer 40 or the separate impedances mentioned above between lines 44 and 45. This results in a small but appreciable current being drawn from the cell constituted by the container and its electrodes, which stabilises the voltage and prevents uncontrolled drift.

The details of the construction of the container and container-mounting member can of course be varied. For example, the noble metal electrode may be mounted in the side of the container instead of in its bottom, in which the recesses in the container-mounting member will be open-sided and have contacts in their inner sides, so that the container can be slid sideways into the recess to make the necessary contacts. Also, the multiplexer 40 can be incorporated with the or each container-mounting member 10 to form a single unit, obviating the need for leads 44 and 45.

I claim:

1. Apparatus for use in detecting micro-organisms in any one of a plurality of samples of a substance, comprising a plurality of containers for samples, wherein each container includes a first electrode of a noble metal and a second electrode of a different metal insulated from the first electrode, the electrodes being arranged so as to be contactable with a sample in the container and presenting respective contact surfaces externally of the container, a container-mounting member provided with means for receiving and locating each of the containers and with a first set of contacts adapted to engage the external contact surfaces of the noble metal electrodes and with a separate lead from each of the said first set of contacts adapted for connecting the noble metal electrodes to separate terminals of a multiplexing recorder system and with a second set of contacts adapted to make contact with the external contact surfaces of the second electrodes, all said second set of contacts being connected to a common lead adapted for connecting said second electrodes to a common terminal of a multiplexing recorder system, the container-mounting member being a block formed with recesses each of which is adapted to receive and locate an individual container and being provided with one of each of said two sets of contacts, the container-mounting block having attached to its underside a printed circuit board with leads connecting each of said first set of contacts to an individual contact of a multi-way connector and with leads connecting all of said second set of contacts to a common contact of the multi-way connector.

2. Apparatus according to claim 1, wherein each container comprises a body formed at least in part of said different metal, and that part of the container body constituted the respective second electrode.

3. Apparatus according to claim 1, wherein each container has an upwardly domed bottom through which projects a pin made of or coated with noble metal, constituting the first electrode.

4. Apparatus according to claim 1, wherein each container has a pin made of or coated with noble metal projecting through its side and constituting the first electrode.

5. Apparatus according to claim 1 wherein each container has a body of aluminum and the first electrode is constituted by a gold plated pin projecting through the bottom or side of said container.

6. Apparatus according to claim 1, wherein each container comprises a closure, the first and second electrode for each container being provided in the respective container closure to extend therethrough.

7. Apparatus according to claim 1, wherein each container comprises a closure, the first electrode for each container being provided in the respective container closure to extend therethrough.

8. Apparatus according to claim 1, wherein the multiplexing recorder system comprises an analogue to digital multiplexer arranged to feed voltage signals from the noble metal electrodes of each container in turn to a micro-processor which is programmed to test the signal to ascertain whether the voltage has dropped below a predetermined level and if so to display particulars of the container and of the time taken from commencement of test of the sample to the fall in voltage.

* * * * *